United States Patent

Gers-Barlag et al.

Patent Number: 5,876,702
Date of Patent: Mar. 2, 1999

[54] COSMETIC AND DERMATOLOGICAL LIGHT PROTECTION FORMULATIONS IN THE FORM OF O/W MACROEMULSIONS, O/W MICROEMULSIONS OR O/W/O EMULSIONS

[75] Inventors: Heinrich Gers-Barlag, Kummerfeld; Rainer Kröpke, Hamburg, both of Germany

[73] Assignee: Beiersdorf AG, Hamburg, Germany

[21] Appl. No.: 760,094

[22] Filed: Dec. 11, 1996

[30] Foreign Application Priority Data

Dec. 21, 1995 [DE] Germany .................. 195 480 16.3

[51] Int. Cl.[6] .................. A61K 7/42; A61K 7/44; A61K 7/00
[52] U.S. Cl. .................. 424/59; 424/60; 424/400; 424/401; 574/937; 574/938; 574/939
[58] Field of Search .................. 424/59, 60, 400, 424/401; 514/937, 938, 939

[56] References Cited

U.S. PATENT DOCUMENTS 5,552,135 9/1996 Cioca et al. .................. 424/59

*Primary Examiner*—Shelley A. Dodson
*Attorney, Agent, or Firm*—Sprung Kramer Schaefer & Briscoe

[57] ABSTRACT

O/W macroemulsions or O/W microemulsions or O/W/O emulsions having a content of dissolved UV filter substances which are sparingly soluble per se in oil components, in particular 4,4',4"-(1,3,5-triazine-2,4,6-triyltriimino) tris-benzoic acid tris (2-ethylhexyl ester), obtainable by phase inversion technology.

20 Claims, 1 Drawing Sheet

COSMETIC AND DERMATOLOGICAL LIGHT PROTECTION FORMULATIONS IN THE FORM OF O/W MACROEMULSIONS, O/W MICROEMULSIONS OR O/W/O EMULSIONS

The present invention relates to cosmetic and dermatological light protection formulations, in particular skin care cosmetic and dermatological light protection formulations.

BACKGROUND OF THE INVENTION

The damaging effect of the ultraviolet part of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity.

The narrower range around 308 nm is stated as the erythema activity maximum of sunlight.

Numerous compounds are known for protection against UVB radiation, these usually being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the so-called UVA range, it is also important to have available filter substances, since the rays thereof can also cause damage. Thus, it has been proved that UVA radiation leads to damage to the elastic and collagenic fibers of connective tissue, which makes the skin age prematurely, and that it is to be regarded as a cause of numerous phototoxic and photoallergic reactions. The damaging influence of UVB radiation can be intensified by UVA radiation.

However, UV radiation can also lead to photochemical reactions, the photochemical reaction products then intervening in skin metabolism.

Such photochemical reaction products are chiefly free-radical compounds, for example hydroxyl radicals. Undefined free-radical photo-products which are formed in the skin itself can also show uncontrolled secondary reactions because of their high reactivity. However, singlet oxygen, a non-radical excited state of the oxygen molecule, may occur under UV irradiation, as can short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted as ionizing radiation. There is therefore the risk of ionic species also being formed during UV exposure, which then in turn are capable of intervening oxidatively in biochemical processes.

One advantageous UVB filter is 4,4',4"-(1,3,5-triazine-2,4,6-triyltriimino)tris-benzoic acid tris(2-ethylhexyl ester), synonym: 2,4,6-tris[anilino-(p-carbo-2'-ethyl-1'-hexyloxy)]-1,3,5-triazine.

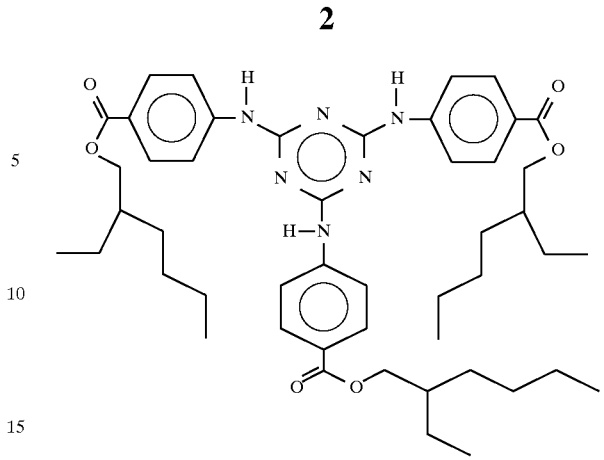

This UVB filter substance is marketed by BASF Aktiengesellschaft under the tradename UVINUL® T 150, and is distinguished by good UV absorption properties.

The main disadvantage of this UVB filter is the poor solubility in lipids. Known solvents for this UVB filter can dissolve not more than about 15% by weight of this filter, corresponding to about 1–1.5% by weight of dissolved, and therefore active, UV filter substance.

Other sparingly soluble UV filter substances are also known, for example 2-phenylbenzimidazole-5-sulphonic acid and its salts, in particular the sodium, potassium and TEA salt, for example obtainable under the name Eusolex® 232 from Merck AG, which is distinguished by the following structural formula:

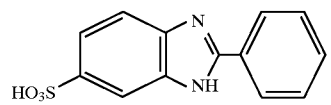

Even if a certain UV protection can be achieved in principle with a given limited solubility (and therefore according to conventional standards: difficulty of incorporation into a cosmetic or dermatological formulation), another problem may occur, that of recrystallization. Precisely in the case of substances of poor solubility, this occurs comparatively rapidly, whether caused by variations in temperature or by other influences. Uncontrolled recrystallization of a substantial constituent of a formulation, such as a UV filter, however, has extremely adverse effects on the properties of the given formulation and, last but not least, on the light protection sought.

It is furthermore known that multiple emulsions—inter alia—can be distinguished by a particularly fine emulsion texture. This property renders them outstandingly suitable as a basis both for cosmetic and for medicinal topical formulations.

In simple emulsions, one phase comprises finely disperse droplets of the second phase enclosed by an emulsifier shell (water droplets in W/O emulsions or lipid vesicles in O/W emulsions). In a multiple emulsion (of the second degree), on the other hand, more finely disperse droplets of the first phase are emulsified in such droplets. In turn, even more finely disperse droplets can also be present in these droplets (multiple emulsion of the third degree) and so on.

Thus, as W/O or O/W emulsions (water-in-oil or oil-in-water) are referred to in the case of simple emulsions, in the case of multiple emulsions there are W/O/W, O/W/O, O/W/O/W, W/O/W/O emulsions and so on.

Multiple emulsions in which the particular internal and external aqueous phases or internal and external oily phases are of a different type (that is to say, for example, W/O/W' and O/W/O' emulsions) can be prepared by two-pot processes. Those emulsions in which the internal and external aqueous and oily phases are not of a different type are obtainable both by one-pot and by two-pot processes.

Multiple emulsions of the second degree are occasionally called "bimultiple systems", those of the third degree are occasionally called "trimultiple systems" and so on (W. Seifriz, Studies in Emulsions, J. Phys. Chem., 29 (1925) 738–749).

The expert is familiar per se with processes for the preparation of multiple emulsions. Thus, there are two-pot processes in which a simple emulsion (for example a W/O emulsion) is initially introduced into the preparation vessel and is converted into a multiple emulsion (for example a W/O/W emulsion) by addition of another phase (for example an aqueous phase) with a corresponding emulsifier (for example an O/W emulsifier).

A second known process comprises converting emulsifier mixtures with an oily phase and an aqueous phase into a multiple W/O/W emulsion in a one-pot process. The emulsifiers are dissolved in the oily phase and the solution is combined with the aqueous phase. A prerequisite for such a process is that the HLB values (HLB=hydrophilic-lipophilic balance) of the individual emulsifiers employed differ significantly from one another.

The definition of the ELB value for polyol fatty acid esters is given by the formula I $$HLB = 20 \times (1 - H/A)$$

For a group of emulsifiers in which the hydrophilic content comprises only ethylene oxide units, formula II applies $$HLB = E/5$$

where

H=hydrolysis number of ester,

A=acid number of the acid recovered

E=weight content of ethylene oxide (in %) in the total molecule.

Emulsifiers with HLB values of 6–8 are in general W/O emulsifiers, and those with HLB values of 8–18 are in general O/W emulsifiers. Literature: "Kosmetik-Entwicklung, Herstellung und Anwendung kosmetischer Mittel" [Cosmetics-Development, Preparation and Use of Cosmetic Compositions]; W. Umbach (editor), Georg Thieme Verlag 1988.

Hydrophilic emulsifiers (with high HLB values) are as a rule O/W emulsifiers. Accordingly, hydrophobic or lipophilic emulsifiers (with low HLB values) are as a rule W/O emulsifiers.

U.S. Pat. No. 4,931,210 describes a process for the preparation of W/O/W emulsions in which polyglycerol polyricinoleates are used as emulsifiers.

The droplet diameters of the usual "simple", that is to say non-multiple, emulsions are in the range from about 1 $\mu$m to about 50 $\mu$m. Without further coloring additives, such "macroemulsions" are milky white in color and opaque. Finer "macroemulsions", the droplet diameters of which are in the range from about $10^{-1}$ $\mu$m to about 1 $\mu$m, again without coloring additives, are bluish white in color and opaque. Such "macroemulsions" usually have a high viscosity.

A clear and transparent appearance is reserved for micellar and molecular solutions with particle diameters of less than about $10^{-2}$ $\mu$m, but these are no longer to be interpreted as true emulsions.

The droplet diameter of microemulsions, on the other hand, is in the range from about $10^{-2}$ $\mu$m to about $10^{-1}$ $\mu$m. Microemulsions are translucent and usually of low viscosity. The viscosity of many microemulsions of the O/W type is comparable to that of water.

An advantage of microemulsions is that active compounds can be present in the disperse phase in a considerably more finely disperse form than in the disperse phase of "macroemulsions". Another advantage is that, because of their low viscosity, they can be sprayed. If microemulsions are used as cosmetics, corresponding products are distinguished by a high cosmetic elegance.

It is known that hydrophilic emulsifiers change their solubility properties from water-soluble to fat-soluble with increasing temperature. The temperature range in which the emulsifiers have changed their solubility is called the phase inversion temperature range (PIT).

S. Matsumoto (Journal of Colloid and Interface Science, Volume 94, No. 2, 1983) reports that the development of a W/O/W emulsion precedes a phase inversion of concentrated W/O emulsions stabilized by Span 80, a pronounced W/O emulsifier. Matsumoto starts here from an extremely non-polar oil, that is to say liquid paraffin. Moreover, a certain amount of hydrophilic emulsifiers is said to be necessary for development of a W/O/W emulsion from a W/O emulsion.

T. J. Lin, H. Kurihara and E. Ohta (Journal of the Society of Cosmetic Chemists 26, pages 121–139, March 1975) show that in the case of non-polar oils, extremely unstable multiple emulsions can be present in the region of the PIT.

DETAILED DESCRIPTION OF THE DRAWINGS

Figure 1:
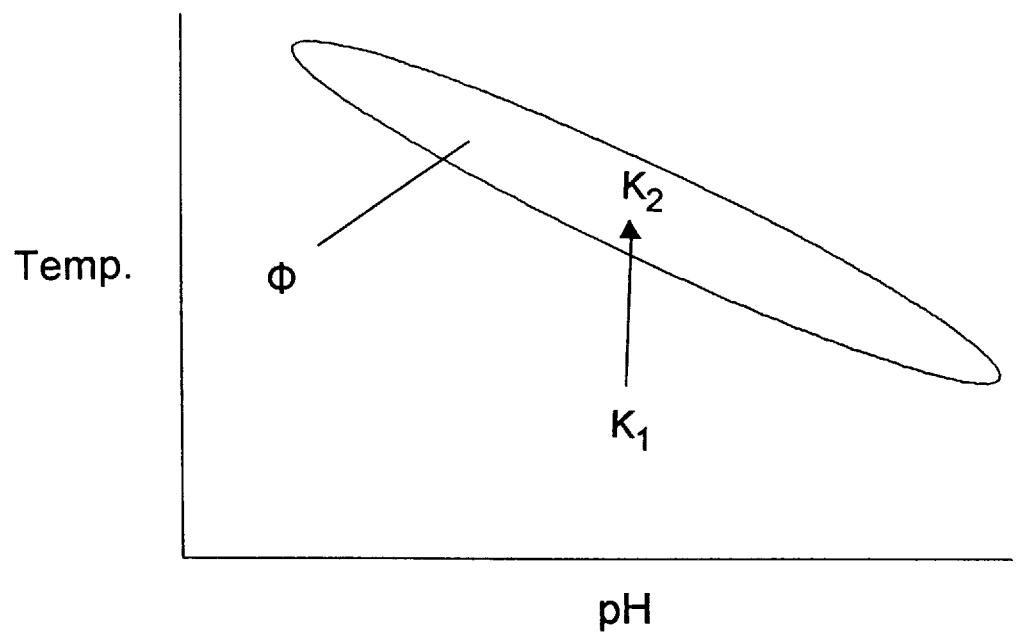

FIG. 1 is a graph showing the phase inversion range which determines mixtures according to the present invention.

DETAILED DESCRIPTION OF THE INVENTION

It has been found, surprisingly, and this accounts for the achievement of the objects, that O/W emulsions, in particular O/W microemulsions, or O/W/O emulsions or O/W/O' emulsions comprising an aqueous phase, if appropriate, customary water-soluble or -dispersible substances, an oily phase, in which a UV filter substance which is sparingly soluble per se in oil components, in particular 4,4', 4"-(1,3,5-triazine-2,4,6-triyl-triimino)-tris-benzoic acid tris(2-ethylhexyl ester) and/or 2-phenylbenzimidazole-5-sulphonic acid or its salts, is present in dissolved form, and at least one emulsifier (emulsifier A) chosen from the group of emulsifiers having the following properties their lipophilicity either depends on the pH such that the lipophilicity is increased or decreased by raising or lowering the pH, it being unimportant which of the two possible changes in lipophilicity is effected by raising or lowering the pH, and/or their lipophilicity depends on the temperature such that the lipophilicity increases with increasing temperature and their hydrophilicity increases with decreasing temperature, and furthermore, if appropriate, further substances which are soluble or dispersible in the oily phase, including, preferably, those chosen from the group of emulsifiers which do not fall under the definition of emulsifier A, in particular those which chiefly act as W/O emulsifiers, remedy the disadvantages of the prior art.

According to the invention, it is possible to achieve high use concentrations of UV filter substances which are sparingly soluble per se in oil components, in particular of 4,4',4"-(1,3,5-triazine-2,4,6-triyltri-imino)tris-benzoic acid tris(2-ethylhexyl ester) and/or of 2-phenylbenzimidazole-5-sulphonic acid or its salts, i.e. typically about 5% by weight, based on the total weight of an O/W microemulsion or an O/W/O emulsion with an oily phase content of about 50% by weight, again based on the total weight of the formulation, and thus to utilize fully the advantageous properties of this light protection filter.

An advantageous embodiment of the present invention is likewise a process for incorporation of UV filter substances which are sparingly soluble per se in oil components, in particular of 4,4',4"-(1,3,5-triazine-2,4,6-triyltriimino)tris-benzoic acid tris(2-ethylhexyl ester) and/or 2-phenylbenzimidazole-5-sulphonic acid or its salts, into emulsions, in particular O/W emulsions, O/W microemulsions or O/W/O emulsions, characterized in that the constituents of an aqueous phase, if appropriate, customary water-soluble or -dispersible substances, the constituents of an oily phase, at least one emulsifier (emulsifier A) chosen from the group of emulsifiers having the following properties
  their lipophilicity either depends on the pH such that the lipophilicity is increased or decreased by raising or lowering the pH, it being unimportant which of the two possible changes in lipophilicity is effected by raising or lowering the pH, and/or
  their lipophilicity depends on the temperature such that the lipophilicity increases with increasing temperature and the hydrophilicity increases with decreasing temperature, UV filter substances which are sparingly soluble per se in oil components, in particular 4,4',4"-(1,3,5-triazine-2,4,6-triyltriimino)tris-benzoic acid tris(2-ethylhexyl ester) and/or 2-phenylbenzimidazole-5-sulphonic acid and its salts, and furthermore, if appropriate, further substances which are soluble or dispersible in the oily phase, including, preferably, those chosen from the group of emulsifiers which do not fall under the definition of emulsifier A, in particular those which chiefly act as W/O emulsifiers, are brought together and, with agitation, a mixture is formed such that by suitable choice of the parameters chosen from the group consisting of pH, temperature and the concentration or concentrations of at least one of the emulsifiers chosen, this mixture is brought into the phase inversion range in which W/O emulsions are converted into O/W emulsions, by varying at least one parameter chosen from the group consisting of pH, temperature and the concentration or concentrations of at least one of the emulsifiers chosen, the W/O emulsion formed is brought out of the phase inversion range in which a W/O emulsion formed is converted into an O/W emulsion, whereupon an O/W emulsion or O/W microemulsion is produced, if appropriate, by suitable choice of the framework conditions, another phase inversion to give an O/W/O emulsion is initiated, if appropriate, the mixture is subjected to further processing steps, in particular one or more homogenizing steps.

If the phase inversion is essentially initiated by varying the temperature, O/W emulsions, in particular O/W microemulsions, are obtainable, the size of the oil droplets essentially being determined by the concentration of the emulsifier or emulsifiers employed such that a higher emulsifier concentration has the effect of smaller droplets and a lower emulsifier concentration leads to larger droplets. If the phase inversion is essentially initiated by varying the temperature, it is entirely advantageous to dispense with further emulsifiers which do not fall under the definition of emulsifier A, that is to say W/O emulsifiers.

If the phase inversion is essentially initiated by varying the pH, O/W emulsions, in particular O/W microemulsions, and also O/W/O emulsions are obtainable. If the phase inversion is essentially initiated by varying the pH, it is entirely advantageous to employ one or more further emulsifiers which do not fall under the definition of emulsifier A, that is to say W/O emulsifiers.

O/W/O emulsions can be obtained according to the invention if the oily phase content is greater than about 15% by weight, in particular greater than about 20% by weight, based on the total weight of the formulation, more than about 5% by weight, in particular about 5–10% by weight, of an additional W/O emulsifier which does not fall under the definition of emulsifier A is present, and/or if the oily phase has a low content of polar oils.

O/W microemulsions can be obtained according to the invention if the oily phase content is less than about 20% by weight, in particular less than about 15% by weight, based on the total weight of the formulation, less than about 5% by weight of an additional W/O emulsifier which does not fall under the definition of emulsifier A is present, and/or if the oily phase has a high content of polar oils.

O/W emulsions ("macroemulsions") can be obtained according to the invention if less than about 5% by weight of an additional W/O emulsifier which does not fall under the definition of emulsifier A and more than about 20% by weight of a polar oily phase are present. Additional gel-forming agents (for example carbopols, xanthan gum, cellulose derivatives) can advantageously be employed.

In the individual case, it is possible that the concentration easily exceeds or falls below the above-mentioned limits, and nevertheless the emulsion types in question are obtained. In view of the wide-ranging diversity of suitable emulsifiers and oil constituents, this is not unexpected to the expert, so that he knows that such excesses or deficits do not leave the basis of the present invention.

It has been found, astonishingly, that the UV filter substance or substances which is or are sparingly soluble per se and is or are employed according to the invention can be stabilized in an outstanding manner in solution, and that recrystallization of insoluble or sparingly soluble UV filter substances can be prevented. Furthermore, light protection formulations which have outstanding use properties are obtainable according to the invention.

Processes which are equally advantageous according to the invention are those in which the variation in the parameter or parameters comprises a procedure in which (a) at a given pH and given concentration of emulsifier A or of the plurality of emulsifiers A, the temperature of the mixture and, if appropriate, additionally the concentration of at least one further emulsifier A is varied, in which (b) at a given temperature and given concentration of emulsifier A or of the plurality of emulsifiers A, the pH of the mixture and, if appropriate, additionally the concentration of at least one further emulsifier A is varied, in which (c) at a given temperature and given pH, the concentration of at least one emulsifier A and, if appropriate, additionally the concentration of at least one further emulsifier A is varied, in which (d) at a given pH, the temperature of the mixture and additionally the concentration of at least one emulsifier A and, if appropriate, additionally the concentration of at least one further emulsifier A are varied, in which (e) at a given temperature of the mixture, the pH of the mixture and additionally the concentration of at least one emulsifier A and, if appropriate, additionally the concentration of at least one further emulsifier A are varied, and in which (f) at a given concentration of at least one emulsifier A, the pH and additionally the temperature of the mixture and, if appropriate, additionally the concentration of at least one further emulsifier A are varied.

The phase inversion range can be demonstrated mathematically as a point quantity within the straightline coordinate system $\Sigma$ formed by the parameters of temperature, pH and concentration of a suitable emulsifier or of an emulsifier mixture in the formulation, in accordance with:

$$\Sigma = \{O, \theta, a, m\}$$

where

O—coordinate origin $\theta$—temperature a—pH m—concentration

In precise terms, in a multi-component emulsifier system, the amount mi of each individual emulsifier must of course be taken into account to give the total function, which, in the case of an i-component emulsifier system, leads to the relationship $$\Sigma = \{O, \theta, a, m_1, M_2, \ldots, m_i\}.$$

The phase inversion range $\Phi$ in the mathematical sense here is a continuous region or a plurality of continuous regions within the coordinate system $\Sigma$. $\Phi$ represents the total amount of coordinate points K ($\theta$, a, $m_1$, $m_2$, ..., $m_i$) which determine mixtures according to the invention of an aqueous and oily phase and i emulsifiers according to the invention of concentration $m_i$ at the temperature $\theta$ and the pH a, and for which phase inversion occurs on transition from one coordinate $K_1 \notin \Phi$ to a coordinate $K_2 \in \Phi$, as described in FIG. 1. The temperature and pH of a given mixture keeping the concentration of $m_1$–$m_i$ constant have been shown as variable coordinates in FIG. 1. On transition from $K_1$ to $K_2$, only the temperature is increased.

Under the conditions according to the invention, this process is not necessarily reversible, i.e. if the system reverts from coordinate $K_2 \in \Phi$ back to coordinate $K_1 \notin \Phi$, other types of emulsion than would have been expected from the prior art can be obtained according to the invention. For example, if, by increasing the temperature of a mixture according to the invention of aqueous and oily phase and i emulsifiers according to the invention of concentrations $m_i$, the pH a remaining constant, starting from a temperature which is too low for phase inversion (that is to say conditions where a conventional O/W emulsion would be present and would also remain as such on cooling to room temperature), the system is heated such that phase inversion occurs, after cooling, for example to room temperature, no conventional O/W emulsion but an O/W microemulsion according to the invention is obtained. Alternatively, mutatis mutandis: an O/W/O emulsion according to the invention.

It is unimportant here whether the phase inversion range of a given system is a single continuous (i+2)-dimensional region or comprises several such regions which are continuous but separate from one another, i.e. corresponding to several phase inversion ranges of a given system. In the context of the disclosure submitted here, therefore, one phase inversion range is always referred to as a generalization, even if two or more such ranges which are separate from one another exist.

The practice of preparation of an emulsion according to the invention advantageously comprises a procedure in which, after selection of suitable raw materials, i.e. the aqueous and oily phase, one or more emulsifiers of type A, the latter present in concentrations at which phase inversion for the given mixture is possible, and, if appropriate, further substances, the individual components are heated, with agitation, to a temperature at which phase inversion is possible for the given mixture, and phase inversion is brought about by raising or lowering the pi of the mixture, after which the mixture is allowed to cool to room temperature, while continuing agitation. One or more intermediate homogenization steps are advantageous but not absolutely necessary.

Another advantageous embodiment of the process according to the invention comprises a procedure in which, after selection of suitable raw materials, i.e. the aqueous and oily phase, one or more emulsifiers of type A, the latter present in concentrations at which phase inversion for the given mixture is possible, and, if appropriate, further substances, the individual components are brought, with agitation, to a pH at which phase inversion is possible for the given mixture, and phase inversion is brought about by increasing the temperature of the mixture, after which the mixture is allowed to cool to room temperature, while continuing agitation. One or more intermediate homogenization steps are advantageous but not absolutely necessary.

A third advantageous embodiment of the process according to the invention comprises a procedure in which, after selection of suitable raw materials, i.e. the aqueous and oily phase, one or more emulsifiers of type A and, if appropriate, further substances, the individual components are brought, with agitation, to a pH and a temperature at which phase inversion is possible for the given mixture, and phase inversion is brought about by addition of emulsifier A or emulsifiers A to the mixture, after which the mixture is allowed to cool to room temperature, while continuing agitation. One or more intermediate homogenization steps are advantageous but not absolutely necessary.

In practice, it is possible and, where appropriate, even advantageous for the temperature range which can be assigned to the phase inversion range also to be exceeded during preparation of an emulsion according to the invention, since the mixture necessarily passes through this range on cooling to room temperature.

In principle, it is possible and advantageous to add the UV filter substances which are sparingly soluble per se in oil components, in particular 4,4',4"-(1,3,5-triazine-2,4,6-triyltriimino)tris-benzoic acid tris(2-ethylhexyl ester), to the mixture on which the emulsions are based at any desired point in time. However, it is preferable for this substance already to be dissolved in a polar oil or a mixture of polar oils before the emulsifying operation and only then to start the process according to the invention. Nevertheless, where appropriate, it is advantageous to dissolve the 4,4",4"-(1,3,5-triazine-2,4,6-triyltriimino)trio-benzoic acid tris(2-ethylhexyl ester) in the polar oily phase, with heating.

The emulsifies A are preferably chosen from the group consisting of emulsifiers which are good proton donors or proton acceptors, where it must be ensured that their lipophilicity either depends on the pH such that the lipophilicity is increased or decreased by raising or lowering the pH, it being unimportant which of the two possible changes in lipophilicity is effected by raising or lowering the pH, or their lipophilicity depends on the temperature such that the lipophilicity increases with increasing temperature and the hydrophilicity thereof increases with decreasing temperature, or their lipophilicity depends on the pH and the temperature such that the lipophilicity is increased or decreased by raising or lowering the pH, it being unimportant which of the two possible changes in lipophilicity is effected by raising or lowering the pH, and that the lipophilicity increases with increasing temperature and the hydrophilicity thereof increases with decreasing temperature.

The emulsifiers of type A are advantageously chosen from the group consisting of sorbitan esters and sucrose esters, in particular of branched and unbranched alkyl esters and alkenyl esters having carbon chains of 4–24 carbon atoms, preferably sorbitan stearate, sorbitan oleate, glycerylsorbitan stearate, sucrose monostearate, sucrose monolaurate and sucrose palpitate.

The emulsifiers of type A can advantageously be chosen from the group consisting of monoglycerol monocarboxylic acid monoesters, in particular those which are characterized by the structures

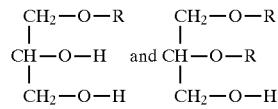

wherein R is a branched or unbranched acyl radical having 6–14 carbon atoms. R is advantageously chosen from the group consisting of unbranched acyl radicals. The fatty acids or monocarboxylic acids on which these esters are based are

| hexanoic acid (caproic acid) | (R = —C(O)—$C_5H_{11}$), |
| heptanoic acid (oenanthic acid) | (R = —C(O)—$C_6H_{13}$), |
| octanoic acid (caprylic acid) | (R = —C(O)—$C_7H_{15}$), |
| nonanoic acid (pelargonic acid) | (R = —C(O)—$C_8H_{17}$), |
| decanoic acid (capric acid) | (R = —C(O)—$C_9H_{19}$), |
| undecanoic acid | (R = —C(O)—$C_{10}H_{21}$), |
| dodecanoic acid (lauric acid) | (R = —C(O)—$C_{11}H_{23}$), |
| tridecanoic acid | (R = —C(O)—$C_{12}H_{25}$), |
| tetradecanoic acid (myristic acid) | (R = —C(O)—$C_{13}H_{27}$). |

R is particularly advantageously the octanoyl radical (caprylic acid radical) or the decanoyl radical (capric acid radical), that is to say is represented by the formulae

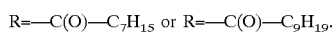

Advantageously, the emulsifiers of type A can also be chosen from the group consisting of di- and triglycerol monocarboxylic acid monoesters. According to the invention, the di- or triglycerol units of the diglycerol monocarboxylic acid monoesters or triglycerol monocarboxylic acid monoesters according to the invention are present as linear, unbranched molecules, that is to say "monoglycerol molecules" etherified via the particular OH groups in the 1- and 3-position.

A small content of cyclic di- or triglycerol units and glycerol molecules etherified via the OH groups in the 2-position can be tolerated. However, it is advantageous to keep such impurities as low as possible.

The monocarboxylic acid monoesters according to the invention are preferably characterized by the following structure:

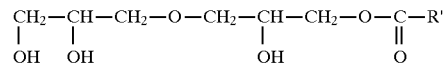

wherein R' is a hydrocarbon radical, advantageously a branched or unbranched alkyl or alkenyl radical having 5 to 17 C atoms.

The triglycerol monocarboxylic acid esters according to the invention are preferably characterized by the following structure:

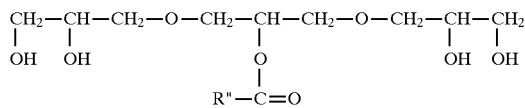

wherein R" is a hydrocarbon radical, advantageously a branched or unbranched alkyl or alkenyl radical having 5 to 17 C atoms.

The acids on which these esters are based are

| hexanoic acid (caproic acid) | (R' or R" = —$C_5H_{11}$), |
| heptanoic acid (oenanthic acid) | (R' or R" = —$C_6H_{13}$), |
| octanoic acid (caprylic acid) | (R' or R" = —$C_7H_{15}$), |
| nonanoic acid (pelargonic acid) | (R' or R" = —$C_8H_{17}$), |
| decanoic acid (capric acid) | (R' or R" = —$C_9H_{19}$), |
| undecanoic acid | (R' or R" = —$C_{10}H_{21}$), |
| 10-undecenoic acid (undecylenic acid) | (R' or R" = —$C_{10}H_{19}$), |
| dodecanoic acid (lauric acid) | (R' or R" = —$C_{11}H_{23}$), |
| tridecanoic acid | (R' or R" = —$C_{12}H_{25}$), |
| tetradecanoic acid (myristic acid) | (R' or R" = —$C_{13}H_{27}$), |
| pentadecanoic acid | (R' or R" = —$C_{14}H_{29}$), |
| hexadecanoic acid (palmitic acid) | (R' or R" = —$C_{15}H_{31}$), |
| heptadecanoic acid (margaric acid) | (R' or R" = —$C_{16}H_{33}$), |
| octadecanoic acid (stearic acid) | (R' or R" = —$C_{17}H_{35}$). |

R' and R" are particularly favorably chosen from the group consisting of unbranched alkyl radicals having odd C numbers, in particular having 9, 11 and 13 C atoms.

The monocarboxylic acid monoesters of diglycerol are generally preferable to those of triglycerol.

Especially favorable according to the invention are

| diglycerol monocaprate (DMC) | R' = 9 |
| triglycerol monolaurate (TML) | R" = 11 |
| diglycerol monolaurate (DML) | R' = 11 |
| triglycerol monomyristate (TMM) | R' = 13. |

Diglycerol monocaprate (DMC) has proved to be the preferred diglycerol monocarboxylic acid monoester according to the invention.

According to an advantageous embodiment of the present invention, an additional content of di- or triglycerol esterified at other points, and also optionally a content of the various diesters of di- or triglycerol, are used.

Triglyceryl diisostearate (nomenclature analogous to CTFA: polyglyceryl 3-diisostearate), isostearyldiglyceryl succinate, diglyceryl sesquiisostearate (nomenclature analogous to CTFA: polyglyceryl 2-sesquiisostearate), triglyceryl polyhydroxystearate (nomenclature analogous to CTFA: polyglyceryl 2-polyhydroxystearate) are also advantageous.

Cetearyl isononanoate, dicocoyl-pentaerythrityl distearyl citrate, also the methicone copolyols, cyclomethicone copolyols, alkylmethicone copolyols, especially laurylmethicone copolyol, cetyldimethicone copolyol, have also proved advantageous according to the invention.

The emulsifier or emulsifiers of type A are especially advantageously chosen from the group consisting of branched or unbranched alkylmonocarboxylic acids, alkenylmonocarboxylic acids and alkylenedicarboxylic acids having 4 to 30 carbon atoms, in particular stearic acid, oleic acid, succinic acid, hexanoic acid (caproic acid), heptanoic acid (oenanthic acid), octanoic acid (caprylic acid), nonanoic acid (pelargonic acid), decanoic acid (capric acid), undecanoic acid, undecenoic acid (undecylenic acid), dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), isostearic acid and behenic acid. It is also advantageous to choose the emulsifiers A from the group consisting of cosmetically or pharmaceutically acceptable salts of the abovementioned carboxylic acids, in particular the alkali metal, ammonium, monoalkylammonium, dialkylammonium, trialkylammonium and tetraalkylammonium salts.

The emulsions according to the invention are advantageously characterized in that the emulsifier A or the emulsifiers A is or are present in concentrations of 0.01–20% by weight, preferably 0.05–10% by weight, particularly preferably 0.1–5% by weight, in each case based on the total weight of the composition.

It is possible according to the invention for the amounts of 4,4',4"-(1,3,5-triazine-2,4,6-triyltriimino)-tris-benzoic acid tris(2-ethylhexyl ester) employed in cosmetic or dermatological formulations to be increased up to threefold compared with the prior art.

It was furthermore astonishing that, by addition of salicylic acid derivatives according to the invention, stabilization of solutions of 4,4',4"-(1,3,5-triazine-2,4,6-triyltriimino)tris-benzoic acid tris(2-ethylhexyl ester) is effected, since the latter substance not only has a poor solubility but also readily crystallizes out of its solution again. The invention therefore also relates to a process for stabilizing solutions of 4,4',4"-(1,3,5-triazine-2,4,6-triyltriimino)tris-benzoic acid tris(2-ethylhexyl ester) in an oily phase, characterized in that such solutions are present in O/W microemulsions or O/W/O emulsions.

A process which is particularly advantageous in the context of the present invention is one for stabilizing solutions of UV filter substances which are sparingly soluble per se in oil components, in particular of 4,4',4"-(1,3,5-triazine-2,4,6-triyltriimino)tris-benzoic acid tris(2-ethylhexyl ester), in an oily phase, characterized in that the 4,4',4"-(1,3,5-triazine-2,4,6-triyltriimino)tris-benzoic acid tris(2-ethylhexyl ester) is incorporated into an O/W microemulsion or O/W/O emulsion such that the constituents of an aqueous phase,
if appropriate, customary water-soluble or -dispersible substances,
the constituents of an oily phase,
at least one emulsifier (emulsifier A) chosen from the group of emulsifiers having the following properties
their lipophilicity either depends on the pH such that the lipophilicity increases or decreases by increasing or lowering the pH, it being unimportant which of the two possibilities of the change in lipophilicity is caused by increasing or lowering the pH, and/or
their lipophilicity depends on the temperature such that the lipophilicity increases with increasing temperature and the hydrophilicity increases with decreasing temperature,
UV filter substances which are sparingly soluble per se in oil components, in particular 4,4',4"-(1,3,5-triazine-2, 4,6-triyltriimino)tris-benzoic acid tris(2-ethylhexyl ester) and/or 2-phenylbenzimidazole-5-sulphonic acid and its salts,
and furthermore, if appropriate, further substances which are soluble or dispersible in the oily phase, including, preferably, those chosen from the group of emulsifiers which do not fall under the definition of emulsifier A, in particular those which chiefly act as W/O emulsifiers, are brought together and, with agitation, a mixture is formed such that by suitable choice of the parameters chosen from the group consisting of pH, temperature and the concentration or concentrations of at least one of the emulsifiers chosen, this mixture is brought into the phase inversion range in which W/O emulsions are converted into O/W emulsions, by varying at least one parameter chosen from the group consisting of pH, temperature and the concentration or concentrations of at least one of the emulsifiers chosen, the W/O emulsion formed is brought out of the phase inversion range in which a W/O emulsion formed is converted into an O/W emulsion, whereupon an O/W emulsion or O/W microemulsion is produced, if appropriate, by suitable choice of the framework conditions, another phase inversion to give an O/W/O emulsion is initiated, if appropriate, the mixture is subjected to further processing steps, in particular one or more homogenizing steps.

Particular preferred formulations according to the invention are those which comprise, as further UV protection substances, salicylic acid derivatives, for example 4-isopropylbenzyl salicylate, 2-ethylhexyl salicylate (octyl salicylate) and/or homomenthyl salicylate, in particular those salicylic acid derivatives of the general structure

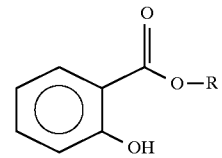

wherein R can be:

(1) a branched or unbranched alkyl radical having 5–18 carbon atoms or (2) an unsubstituted cycloalkyl radical having 5–7 carbon atoms or (3) a cycloalkyl radical having 5 to 7 carbon atoms which is substituted by up to 10 branched or unbranched alkyl radicals having 5–18 carbon atoms or (4) an unsubstituted phenyl radical or (5) a phenyl radical which is substituted by up to 5 branched or unbranched alkyl radicals having 5–18 carbon atoms.

Customary UV filters include, among others,

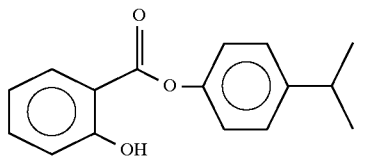

(4-isopropylbenzyl salicylate)

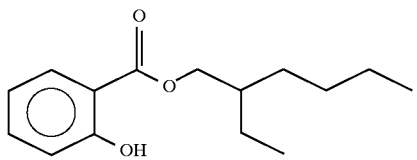

(2-ethylhexyl salicylate, octyl salicylate)

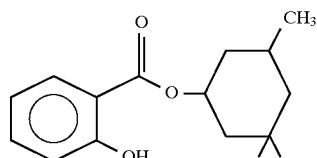

(homomenthyl salicylate).

The total amount of UV filter substances which are sparingly soluble per se in oil components, in particular 4,4',4"-(1,3,5-triazine-2,4,6-triyltriimino)-tris-benzoic acid tris(2-ethylhexyl ester), in the finished cosmetic or dermatological formulations is advantageously chosen from the range of 0.1–10.0% by weight, preferably 0.5–6.0% by weight, based on the total weight of the formulations.

The total amount of one or more salicylic acid derivatives according to the invention in the finished cosmetic or dermatological formulations is advantageously chosen from the range of 0.1–10.0% by weight, preferably 0.5–6.0% by weight, based on the total weight of the formulations.

It is advantageous to choose weight ratios of 4,4',4"-(1, 3,5-triazine-2,4,6-triyltriimino)tris-benzoic acid tris(2-ethylhexyl ester) and one or more salicylic acid derivatives according to the invention from the range of from 1:10 to 10:1, preferably 1:4 to 4:1.

It is advantageous according to the invention to employ further oil-soluble UVA filters and/or UVB filters in the lipid phase and/or water-soluble UVA filters and/or UVB filters in the aqueous phase in the formulations according to the invention.

The light protection formulations according to the invention can advantageously comprise further substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation.

The UVB filters can be oil-soluble or water-soluble. Advantageous oil-soluble UVB filter substances are, for example:
  3-benzylidenecamphor derivatives, preferably 3-(4-methylbenzylidene)camphor and 3-benzylidenecamphor;
  4-aminobenzoic acid derivatives, preferably 2-ethylhexyl 4-(dimethylamino)benzoate and amyl 4-(dimethylamino)benzoate;
  esters of cinnamic acid, preferably 2-ethylhexyl 4-methoxycinnamate and isopentyl 4-methoxycinnamate;
  derivatives of benzophenone, preferably 2-hydroxy-4-methoxybenzophenone, 2-hydroxy-4-methoxy-4'-methylbenzophenone and 2,2'-dihydroxy-4-methoxybenzophenone;
  esters of benzalmalonic acid, preferably di(2-ethylhexyl) 4-methoxybenzalmalonate.

Advantageous water-soluble UVB filter substances are, for example:
  salts of 2-phenylbenzimidazole-5-sulphonic acid, such as its sodium, potassium or its triethanolammonium salt, and the sulphonic acid itself;
  sulphonic acid derivatives of benzophenones, preferably 2-hydroxy-4-methoxybenzophenone-5-sulphonic acid and salts thereof;
  sulphonic acid derivatives of 3-benzylidenecamphor, such as, for example, 4-(2-oxo-3-bornylideneirethyl)-benzenesulphonic acid, 2-methyl-5-(2-oxo-3-bornylidenemethyl) benzenesulphonic acid and salts thereof.

The list of UVB filters mentioned which can be used in combination with the active compound combinations according to the invention is not of course intended to be limiting.

It may also be advantageous to employ in the formulations according to the invention UVA filters which have usually been contained to date in cosmetic formulations. These substances are preferably derivatives of dibenzoylmethane, in particular 1-(4'-tert-butylphenyl)-3-(4'-methoxyphenyl)propane-1,3-dione and1-phenyl-3-(4'-isopropylphenyl)propane-1,3-dione. The invention also relates to these combinations and to formulations which comprise these combinations. The amounts used for the UVB combination can be employed.

It is furthermore advantageous to combine the active compound combinations according to the invention with further UVA and/or UVB filters.

Cosmetic and dermatological formulations according to the invention advantageously also comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminum ($Al_2O_3$) or cerium (for example $Ce_2O_3$), mixed oxides of the corresponding metals and mixtures of such oxides. The pigments are particularly preferably those based on $TiO_2$.

It is particularly advantageous in the context of the present invention, although not absolutely necessary, if the inorganic pigments are present in a hydrophobic form, i.e. they have been given a water-repellent treatment on the surface. This surface treatment can comprise providing the pigments with a thin hydrophobic layer by processes known per se.

Such a process comprises, for example, a procedure in which the hydrophobic surface layer is produced by a reaction according to n $TiO_2$+m $(RO)_3$ Si—R'→n $TiO_2$ (surface). n and m here are stoichiometric parameters to be employed as desired and R and R' are the desired organic radicals. Hydrophobized pigments prepared analogously to DE-OS 33 14 742, for example, are advantageous.

Advantageous $TiO_2$ pigments are obtainable, for example, under the tradenames MT 100 T from TAYCA.

The cosmetic and/or dermatological light protection formulations according to the invention can have the customary composition and be used for cosmetic and/or dermatological light protection, and furthermore for the treatment, care and cleansing of the skin and/or hair and as a make-up product in decorative cosmetics.

For use, the cosmetic and dermatological formulations according to the invention are applied to the skin and/or the hair in an adequate amount in the manner customary for cosmetics.

Those cosmetic and dermatological formulations which are present in the form of a sunscreen composition are particularly preferred. These can advantageously additionally comprise at least one further UVA filter and/or at least one further UVB filter and/or at least one inorganic pigment, preferably an inorganic micropigment.

The cosmetic and dermatological formulations according to the invention can comprise cosmetic auxiliaries such as are usually used in such formulations, for example preservatives, bactericides, perfumes, substances for preventing foaming, dyestuffs, pigments which have a coloring action, thickeners, humidifying and/or humectant substances, fats, oils, waxes or other customary constituents of a cosmetic or dermatological formulation, such as alcohols, polyols, polymers, foam stabilizers, electrolytes, organic solvents or silicone derivatives.

An additional content of antioxidants is in general preferred. All the antioxidants suitable or customary for cosmetic and/or dermatological uses can be used according to the invention as favorable antioxidants.

The antioxidants are advantageously chosen from the group consisting of amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene, lycopene) and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones, penta-, hexa- and heptathionine-sulphoximine) in very low tolerated dosages (for example pmol to $\mu$mol/kg), and furthermore (metal)chelating agents (for example α-hydroxy-fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives (for example ascorbyl palmitate, Mg ascorbyl phosphate, ascorbyl acetate), tocopherols and derivatives (vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO, $ZnSO_4$), selenium and derivatives thereof (for example selenium methionine), stilbenes and derivatives thereof (for example stilbene oxide, trans-stilbene oxide) and the derivatives of these active compounds mentioned which are suitable according to the invention (salts, esters, ethers, sugars, nucleotides, nucleosides, peptides and lipids).

The amount of the abovementioned antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof is or are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof is or are the antioxidant or antioxidants, it is advantageous to choose the particular concentrations thereof from the range of 0.001–10% by weight, based on the total weight of the formulation.

The lipid phase can advantageously be chosen from the following group of substances:

oils, such as triglycerides of capric or of caprylic acid, but preferably castor oil;

fats, waxes and other naturally occurring and synthetic fat substances, preferably esters of fatty acids with alcohols of low C number, for example with isopropanol, propylene glycol or glycerol, or esters of fatty alcohols with alkanoic acids of low C number or with fatty acids;

alkyl benzoates; and silicone oils, such as dimethylpolysiloxanes, diethylpolysiloxanes, diphenylpolysiloxanes and mixed forms thereof.

If appropriate, the aqueous phase of the formulations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols of low C number, for example ethanol, isopropanol, 1,2-propanediol and glycerol, and, in particular, one or more thickeners, which can advantageously be chosen from the group consisting of silicon dioxide, aluminum silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of so-called carbopols, for example carbopols of types 980, 981, 1382, 2984 and 5984, in each case individually or in combination.

The cosmetic or dermatological light protection formulations advantageously comprise inorganic pigments, in particular micropigments, for example in amounts of 0.1% by weight to 30% by weight, preferably in amounts of 0.5% to 10% by weight, but in particular 1% to 6% by weight, based on the total weight of the formulations.

Some peculiarities and differences in the prerequisites of O/W emulsions, O/W microemulsions and O/W/O emulsions according to the invention will also be briefly discussed below.

Oils and fats differ, inter alia, in their polarity, which is difficult to define. It has already been proposed to adopt the surface tension with respect to water as a measure of the polarity index of an oil or of an oily phase. In this case, the polarity of the oily phase in question is greater, the lower the surface tension between this oily phase and water. According to the invention, the surface tension is regarded as a possible measure of the polarity of a given oil component.

The surface tension is that force which acts on an imaginary line of one metre in length in the interface between two phases. The physical unit for this surface tension is conventionally calculated from the relationship force/length and is usually expressed in mN/m (millinewtons divided by metres). It has a positive sign if it endeavors to reduce the interface. In the converse case, it has a negative sign.

According to the invention, the limit below which an oily phase is "polar" and above which an oily phase is "non-polar" is regarded as 30 mN/m.

According to the invention, the oily phase for O/W microemulsions is advantageously chosen from the group consisting of polar oil components which have a polarity of between 10 and 30 mN/m, where it must be ensured that at least one non-polar oil component is present.

Advantageous O/W microemulsions are obtained if the oily phase is chosen from the group consisting of polar oil components, particularly preferably the group consisting of naturally occurring, synthetic or semi-synthetic oil components which have a polarity of between 10 and 20 mN/m, where it must be ensured that at least one non-polar oil component is present.

It is also advantageous to use polar vegetable oils as polar oils of the O/W emulsions according to the invention. The vegetable oils can advantageously be chosen from the group consisting of oils of the plant families Euphorbiaceae, Poaceae, Fabaceae, Brassicaceae, Pedalaceae, Asteraceae, Linaceae, Flacourticaceae and Violales, preferably chosen from the group consisting of natural castor oil, wheat germ oil, grapeseed oil, candlenut oil, safflower oil, thistle oil, oil of evening primrose and other oils which comprise at least 1.5% by weight of linoleic acid glycerides.

In contrast, O/W/O emulsions according to the invention should have only minor amounts of such oil components, and instead of these should have chiefly those of which the polarity value is higher than 30 mN/m. Naturally occurring, synthetic and semi-synthetic oils, fats and waxes have similarly proved to be advantageous.

The addition of electrolytes causes a change in the solubility properties of a hydrophilic emulsifier. The hydrophilic emulsifiers having the structures or properties described above pass through a partial phase inversion in which solubilization of water by the oily phase occurs, resulting in a stable microemulsion or, in the desired case, also a stable O/W/O emulsion.

The microemulsions according to the invention therefore advantageously comprise electrolytes, in particular one or more salts with the following anions: chlorides, and furthermore inorganic oxo element anions, and of these in particular sulphates, carbonates, phosphates, borates and aluminates. Electrolytes based on organic anions can also advantageously be used, for example lactates, acetates, benzoates, propionates, tartrates, citrates and many others. Comparable effects can also be achieved by ethylenediaminetetraacetic acid and salts thereof.

Cations of the salts which are preferably used are ammonium, alkylammonium, alkali metal, alkaline earth metal, magnesium, iron and zinc ions. It does not need mentioning that only physiologically acceptable electrolytes should be used in cosmetics. On the other hand, specific medicinal uses of the microemulsions according to the invention may at least in principle require the use of electrolytes which should not be used without medical supervision.

Potassium chloride, sodium chloride, magnesium sulphate, zinc sulphate and mixtures thereof are particularly preferred. Salt mixtures such as occur in the natural salt of the Dead Sea are likewise advantageous.

The concentration of the electrolyte or electrolytes should be about 0.01–10.0% by weight, particularly advantageously about 0.03–8.0% by weight, based on the total weight of the formulation.

The emulsifiers of type A can customarily be regarded as O/W emulsifiers. A content of about 5–10% by weight of the usual W/O emulsifiers advantageously promotes the formation of O/W/O emulsions, and a content of significantly more than 10% by weight of such emulsifiers leads to destabilization of the O/W/O emulsions.

If desired, for the preparation of O/W/O emulsions according to the invention, it is furthermore advantageous to employ hydrophilic and/or lipophilic gel-forming agents. Although these as a rule do not contribute towards the formation of multiple droplets, they promote the stability of multiple drops once formed.

If the pH is to be varied in a preparation process according to the invention for O/W/O emulsions, in order to bring an otherwise predetermined system into the phase inversion range, it is advantageous initially to employ the lowest possible electrolyte concentration in the aqueous phase at the start of the process, and if possible initially to omit this concentration entirely. It is furthermore advantageous for emulsifier A to be initially introduced into the oily phase, for example for stearic acid in the concentration range of 0.5–5% by weight, in particular 2% by weight. The presence of an emulsifier which does not fall under the definition of emulsifier A in the concentration range of about 5–10% by weight, in particular about 7% by weight, is advantageous.

The pH should advantageously first be varied when the W/O emulsion has formed, for example by addition of NaOH.

It lies here within the general expertise of the expert and requires no inventive step at all to determine the temperature or pH range in which phase inversion takes place for a given emulsifier or a given emulsifier system in a given aqueous/oily phase system. As a general guideline for the PIT at the usual emulsifier concentrations, a temperature range of about 40°–90° C. can be stated. In general, the PIT drops as the emulsifier concentration increases.

During this process, if desired, the base substances, auxiliaries, additives and/or active compounds customary in cosmetics or medicine formulation can furthermore be added. It is clear to the expert at what point in time such substances can be added to the process without the properties of the emulsion to be achieved being substantially impaired.

The following examples are intended to outline the essence of the present invention in more detail without limiting the invention.

EXAMPLE 1

| O/W microemulsion | |
|---|---|
| | % by weight |
| Ceteareth-12 | 8.00 |
| Cetearyl isononanoate | 20.00 |
| Cetearyl alcohol | 4.00 |
| Uvinul ® T 150 | 2.00 |
| Parsol ® 1789 | 1.00 |
| Eusolex ® 232 | 4.80 |
| | pH = 7.5 |
| Dyestuffs, perfume, preservative | q.s. |
| Water | to 100.00 |

The UV filter is dissolved in the oily phase and combined with the other constituents of the oily phase, after which the mixture is homogenized, subsequently combined with the aqueous phase and brought to a temperature of 80°–85° C. (i.e. in the phase inversion temperature range of the system), and the system is then cooled to room temperature (that is to say is brought out of the phase inversion temperature range of the system again).

EXAMPLE 2

| O/W microemulsion | |
|---|---|
| | % by weight |
| Ceteareth-12 | 12.00 |
| Cetearyl isononanoate | 20.00 |
| Cetearyl alcohol | 6.00 |
| Uvinul ® T 150 | 2.00 |
| Eusolex ® 6300 | 3.00 |
| Eusolex ® 232 | 4.80 |
| | pH = 7.5 |
| Dyestuffs, perfume, preservative | q.s. |
| Water | to 100.00 |

The UV filter is dissolved in the oily phase and combined with the other constituents of the oily phase, after which the mixture is homogenized, subsequently combined with the aqueous phase and brought to a temperature of 80°–85° C. (i.e. in the phase inversion temperature range of the system), and the system is then cooled to room temperature (that is to say is brought out of the phase inversion temperature range of the system again).

EXAMPLE 3

| O/W microemulsion | |
|---|---|
| | % by weight |
| Ceteareth-12 | 8.00 |
| Cetearyl isononanoate | 20.00 |
| Cetearyl alcohol | 4.00 |
| Uvinul ® T 150 | 4.80 |
| MgSO$_4$ | 3.00 |
| Dyestuffs, perfume, preservative | q.s. |
| Water | to 100.00 |

The UV filter is dissolved in the oily phase and combined with the other constituents of the oily phase, after which the mixture is homogenized, subsequently combined with the aqueous phase and brought to a temperature of 80°–85° C. (i.e. in the phase inversion temperature range of the system), and the system is then cooled to room temperature (that is to say is brought out of the phase inversion temperature range of the system again).

EXAMPLE 4

| O/W microemulsion | |
|---|---|
| | % by weight |
| Ceteareth-12 | 12.00 |
| Cetearyl isononanoate | 20.00 |
| Cetearyl alcohol | 6.00 |
| Uvinul ® T 150 | 4.80 |
| Parsol ® 1789 | 2.00 |
| TiO$_2$ | 2.00 |
| MgSO$_4$ | 3.00 |
| Dyestuffs, perfume, preservative | q.s. |
| Water | to 100.00 |

The UV filter is dissolved in the oily phase and combined with the other constituents of the oily phase, after which the mixture is homogenized, subsequently combined with the aqueous phase and brought to a temperature of 80°–85° C. (i.e. in the phase inversion temperature range of the system), and the system is then cooled to room temperature (that is to say is brought out of the phase inversion temperature range of the system again).

EXAMPLE 5

| O/W microemulsion | |
|---|---|
| | % by weight |
| Ceteareth-12 | 8.00 |
| Cetearyl isononanoate | 10.00 |
| Cetearyl alcohol | 4.00 |
| Eusolex ® 232 | 5.00 |
| Uvinul ® T 150 | 1.00 |
| Parsol ® 1789 | 4.00 |
| | pH = 7.5 |
| Dyestuffs, perfume, preservative | q.s. |
| Water | to 100.00 |

The UV filter is dissolved in the oily phase and combined with the other constituents of the oily phase, after which the mixture is homogenized, subsequently combined with the aqueous phase and brought to a temperature of 80°–85° C. (i.e. in the phase inversion temperature range of the system), and the system is then cooled to room temperature (that is to say is brought out of the phase inversion temperature range of the system again).

EXAMPLE 6

| O/W/O emulsion | |
|---|---|
| | % by weight |
| Glyceryl isostearate | 4.00 |
| Cetearyl isononanoate | 20.00 |
| Stearic acid | 2.00 |
| Uvinul ® T 150 | 2.00 |
| Parsol ® 1789 | 3.00 |
| NaOH | to pH 7.0 |
| Dyestuffs, perfume, preservative | q.s. |
| Water | to 100.00 |

The insoluble UV filter substance is dissolved in the oily phase and combined with the remainder of the oily phase.

Water is added and the system is heated to about 40° C. NaOH is added until a pH of 7 is reached, and the system is then cooled to room temperature.

We claim:

1. O/W emulsions, O/W microemulsions, O/W/O emulsions or O/W/O' emulsions comprising an aqueous phase, optionally, customary water-soluble or -dispersible substances, and oily phase, in which a UV filter substance which is sparingly soluble in oil components and selected from the group consisting of 4,4',4"-(1,3,5-triazine-2,4,6-triyl-triimino)-tris-benzoic acid tris(2-ethylhexyl ester), 2-phenylbenzimidazole-5-sulphonic acid, mixtures thereof and its salts, is present in dissolved form, and at least one emulsifier (emulsifier A) having the following properties their lipophilicity either depends on the pH such that the lipophilicity is increased or decreased by raising or lowering the pH, it being unimportant which of the two possible changes in lipophilicity is effected by raising or lowering the pH, and/or their lipophilicity depends on the temperature such that the lipophilicity increases with increasing temperature and their hydrophilicity increases with decreasing temperature, and optionally, further emulsifier substances which are soluble or dispersible in the oily phase which do not fall under the definition of emulsifier A.

2. Emulsions according to claim 1, wherein emulsifier A is at least one emulsifier selected from the group consisting of sorbitan esters and sucrose esters of branched and unbranched alkyl esters and alkenyl esters having carbon chains of 4–24 carbon atoms, monoglycerol monocarboxylic acid monoesters, di- and triglycerol monocarboxylic acid monoesters, triglyceryl monocarboxylic acid monoesters, triglyceryl diisostearate, isostearyl-diglyceryl succinate, diglyceryl sesquiisostearate, triglyceryl polyhydroxystearate, cetearyl isononanoate, dicocoyl-pentaerythrityl distearyl citrate, methicone copolyols, cyclomethicone copolyols, alkylmethicone copolyols, laurylmethicone copolyol, cetyldimethicone copolyol, branched or unbranched alkylmonocarboxylic acids, alkenylmonocarboxylic acids and alkylenedicarboxylic acids having 4 to 30 carbon atoms, and cosmetically or pharmaceutically acceptable salts thereof.

3. Emulsions according to claim 2, wherein emulsifier A is at least one emulsifier selected from the group consisting of sorbitan stearate, sorbitan oleate, glycerylsorbitan stearate, sucrose monostearate, sucrose monolaurate, sucrose palmitate, triglyceryl diisostearate, isostearyl-diglyceryl succinate, diglyceryl sesquiisostearate, triglyceryl polyhydroxystearate, cetearyl isononanoate, dicocoyl-pentaerythrityl distearyl citrate, stearic acid, oleic acid, succinic acid, hexanoic acid (caproic acid), heptanoic acid (oenanthic acid), octanoic acid (caprylic acid), nonanoic acid (pelargonic acid), decanoic acid (capric acid), undecanoic acid, 10-undecenoic acid (undecylenic acid), dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), isostearic acid and behenic acid and cosmetically or pharmaceutically acceptable salts thereof.

4. Emulsions according to claim 2, wherein the pharmaceutically acceptable salts include alkali metal, ammonium, monoalkylammonium, dialkylammonium, trialkylammonium and tetraalkylammonium salts.

5. Emulsions according to claim 1, wherein the emulsifier A or the emulsifiers A is or are present in concentrations of 0.01–20% by weight, in each case based on the total weight of the composition.

6. O/W macroemulsions or O/W microemulsions or O/W/O emulsions according to claim 1, wherein the emulsifier A or the emulsifiers A is or are present in concentrations of 0.05–10% by weight, in each case based on the total weight of the composition.

7. Emulsions according to claim 1, wherein the emulsifier A or the emulsifiers A is or are present in concentrations of 0.1–5% by weight, in each case based on the total weight of the composition.

8. Emulsions according to claim 1, wherein the further emulsifier substances which do not fall within the definition of emulsifier A are those which chiefly act as W/O emulsifiers.

9. Emulsions according to claim 1, wherein the emulsions are O/W emulsions, O/W/O emulsions or O/W/O' emulsions.

10. Emulsions according to claim 1, which further include additional UVA and/or UVB filters.

11. Emulsions according to claim 1, which further include effective amounts of cosmetic and/or dermatological acceptable antioxidants.

12. Process for incorporation of UV filter substances which are sparingly soluble in oil components into emulsions comprising bringing together with agitation the constituents of an aqueous phase, optionally, customary water-soluble or -dispersible substances, the constituents of an oily phase, at least one emulsifier (emulsifier A) selected having the following properties their lipophilicity either depends on the pH such that the lipophilicity increased or decreased by raising or lowering the pH, it being unimportant which of the two possible changes in lipophilicity is effected by raising or lowering the pH, and/or their lipophilicity depends on the temperature such that the lipophilicity increases with increasing temperature and the hydrophilicity increases with decreasing temperature, UV filter substances which are sparingly soluble per se in oil components and selected from the group consisting of 4,4',4"-(1,3,5-triazine-2,4,6-triyltriimino)-tris-benzoic acid tris(2-ethylhexyl ester), 2-phenylbenzimidazole-5-sulphonic acid, mixtures thereof and its salts, and optionally, further emulsifier substances which are soluble or dispersible in the oily phase, which do not fall under the definition of emulsifier A, wherein the mixture is formed such that by suitable choice of the parameters selected from the group consisting of pH, temperature and the concentration or concentrations of at least one of the emulsifiers chosen, this mixture is brought into the phase inversion range in which W/O emulsions are converted into O/W emulsions, by varying at least one parameter selected from the group consisting of pH, temperature and the concentration or concentrations of at least one of the emulsifiers chosen, the W/O emulsion formed is brought out of the phase inversion range in which a W/O emulsion formed is converted into an O/W emulsion, whereupon an O/W emulsion or O/W microemulsion is produced, optionally, by suitable choice of the framework conditions, another phase inversion giving an O/W/O emulsion is initiated, optionally, the mixture is subjected to further processing steps.

13. Process according to claim 12, wherein the UV filter substance or substances which is or are sparingly soluble in oil components are already dissolved in a polar oil or a mixture of polar oils before the emulsifying operation and only then is the process according to the invention started.

14. Process according to claim 12, wherein emulsifier A is at least one emulsifier selected from the group consisting of sorbitan esters and sucrose esters of branched and unbranched alkyl esters and alkenyl esters having carbon chains of 4–24 carbon atoms, monoglycerol monocarboxylic acid monoesters, di- and triglycerol monocarboxylic acid monoesters, triglycerol monocarboxylic acid monoesters, triglyceryl diisostearate, isostearyl-diglyceryl succinate, diglyceryl sesquiisostearate, triglyceryl polyhydroxystearate, cetearyl isononanoate, dicocoyl-pentaerythrityl distearyl citrate, methicone copolyols, cyclomethicone copolyols, alkylmethicone copolyols, laurylmethicone copolyol, cetyldimethicone copolyol, branched or unbranched alkylmonocarboxylic acids, alkenylmonocarboxylic acids and alkylenedicarboxylic acids having 4 to 30 carbon atoms, and cosmetically or pharmaceutically acceptable salts thereof.

15. Process according to claim 14, wherein emulsifier A is at least one emulsifier selected from the group consisting of sorbitan stearate, sorbitan oleate, glycerylsorbitan stearate, sucrose monostearate, sucrose monolaurate, sucrose palmitate, triglyceryl diisostearate, isostearyl-diglyceryl succinate, diglyceryl sesquiisostearate, triglyceryl polyhydroxystearate, cetearyl isonnanoate, dicocoyl-pentaerythrityl distearyl citrate, stearic acid, oleic acid, succinic acid, hexanoic acid (carproic acid), heptanoic acid (oenanthic acid), octanoic acid (caprylic acid), nonanoic acid (pelargonic acid), decanoic acid (capric acid), undecanoic acid, 10-undecenoic acid (undecylenic acid), dodecanoic acid (lauric acid), tridecanoic acid, tetradecanoic acid (myristic acid), pentadecanoic acid, hexadecanoic acid (palmitic acid), heptadecanoic acid (margaric acid), octadecanoic acid (stearic acid), isostearic acid and behenic acid and cosmetically or pharmaceutically acceptable salts thereof.

16. Process according to claim 14, wherein the pharmaceutically acceptable salts thereof include alkali metal, ammonium, monoalkylammonium, dialkylammonium, trialkylammonium and tetraalkylammonium salts.

17. Process according to claim 12, wherein the further emulsifier substances which do not fall within the definition of emulsifier A are those which chiefly act as W/O emulsifiers.

18. Process according to claim 12, wherein the further processing step is homogenization.

19. Process according to claim 2, which further include additional UVA and/or UVB filters.

20. Process according to claim 2, which further include effective amounts of cosmetic and/or dermatological acceptable antioxidants.

* * * * *